United States Patent [19]

Storkebaum et al.

[11] Patent Number: 4,749,476
[45] Date of Patent: Jun. 7, 1988

[54] APPARATUS FOR FILTERING PRESSURE SENSITIVE SUBSTANCES OUT OF LIQUID SUSPENSION

[75] Inventors: Christoph Storkebaum, Braunschweig; Uwe Tegtmeier, Wittmar, both of Fed. Rep. of Germany

[73] Assignee: Starcosa GmbH, Braunschweig, Fed. Rep. of Germany

[21] Appl. No.: 904,339

[22] Filed: Sep. 5, 1986

[30] Foreign Application Priority Data

Sep. 6, 1985 [DE] Fed. Rep. of Germany ....... 3531836

[51] Int. Cl.$^4$ .................................................. B01D 29/36
[52] U.S. Cl. ........................................ 210/97; 210/258; 210/321.84; 210/406; 210/416.1
[58] Field of Search ............... 210/86, 104, 258, 321.1, 210/433.2, 406, 416.1, 321.84, 321.65, 651, 97

[56] References Cited

U.S. PATENT DOCUMENTS 3,528,551  9/1970  Herubel ............................. 210/196
3,974,068  8/1976  Ebner et al. ....................... 210/637

FOREIGN PATENT DOCUMENTS 67884    7/1971   Australia .
1138799  1/1983   Canada .
0086539  8/1983   European Pat. Off. .
2430451  2/1980   France .
1209769  10/1970  United Kingdom .
1238401  7/1971   United Kingdom .

Primary Examiner—Richard V. Fisher
Assistant Examiner—Richard Jordan
Attorney, Agent, or Firm—W. G. Fasse; D. H. Kane, Jr.

[57] ABSTRACT

For the separation of suspensions in the form of liquid solid component mixtures with the aid of porous filter membranes or for the separation of suspensions free of solid components into the liquid components with the aid of solution diffusion membranes, a reduced pressure is produced on the permeate side of the membrane. For this purpose the permeate is sucked off by a jet pump and is transferred into a closed circuit flow in which it serves as a drive medium for the jet pump. The apparatus for performing the method includes a membrane filter arrangement (6) with a closed circuit conduit (11) connected to the permeate discharge conduit. A conveying pump (13) and a jet pump (10) as well as a collecting container (12) is arranged in the closed circuit conduit. The permeate discharge conduit is connected with the jet pump.

5 Claims, 1 Drawing Sheet

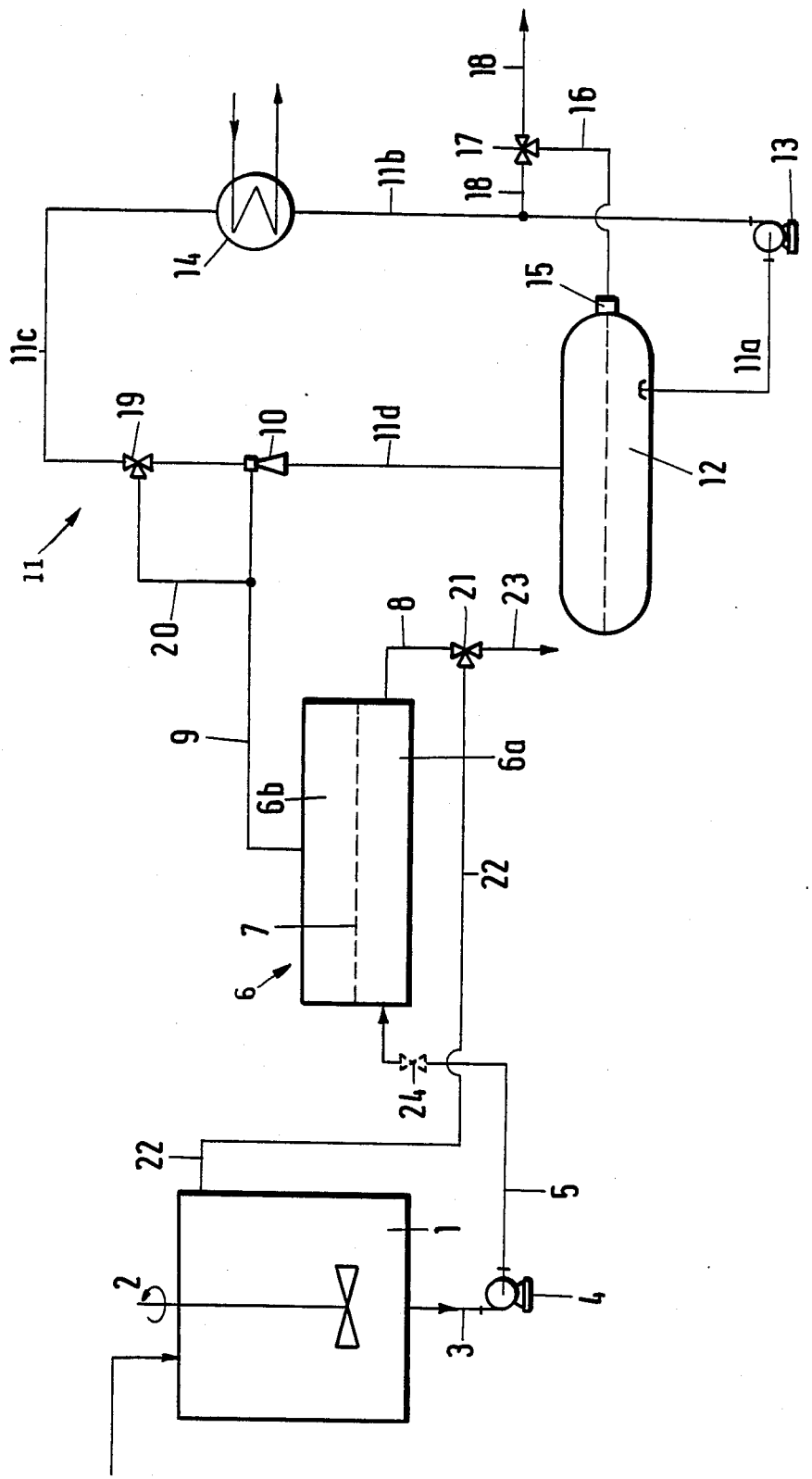

APPARATUS FOR FILTERING PRESSURE SENSITIVE SUBSTANCES OUT OF LIQUID SUSPENSION

The invention relates to a method for separating of suspensions into the individual components, for example the separation of the yeast cells or bacteria out of watery media. The liquid solids mixtures are supplied to filters with porous filter membranes for the separation into solid components and liquid components. Suspensions free of solids are supplied to filters with solution diffusion membranes for separation into the liquid components. A variable pressure difference is adjusted and retained at the respective membranes between the supply side or the retention side on the one hand and the permeate side on the other hand, whereby a higher pressure is maintained on the supply side or the retention side.

The invention also relates to an apparatus for performing the mentioned method.

Methods of the above mentioned type are known in which the higher pressure on the supply side or the retention side of the membrane relative to the permeate side is produced by the effect of gravity in that the suspension is supplied to the supply side or retention side from a level which is higher than that of the membrane.

In other structures the higher pressure on the supply or retention side is produced by respective pumps which supply the suspension to the supply side or the retention side.

The size of the pressure difference between the supply side or retention side on the one hand and the permeate side on the other hand depends on the type and composition of the suspension and on the data of the membrane. For the operation of the membrane a pressure gradient must exist between the supply of the substance to be separated and the exit of the retained component. This pressure gradient depends on the data of the membrane. The pressure gradient comprises a component corresponding to the pressure that must be converted into flow energy for a sufficiently intensive throughflow of the retention space and a component corresponding to the pressure drop that is necessary for the flow through the membrane. The flow through the retention space must have a certain intensity or speed for avoiding the so-called fouling at the membrane. The pressure drop at the membrane on its part must have a certain minimum size which depends on the construction of the membrane and on the throughflow and separation of the permeate out of the supplied substance.

A substantial energy is necessary for the production of the pressure difference comprising the two mentioned components. This energy must be provided either in the form of pump power or by providing a respective high static pressure gradient. Due to the high pressure required on the supply side or on the retention side, it is possible that especially gravity sensitive cells such as animal cells or fungi cultures growing in submersion may be damaged or destroyed.

It is an object of the invention to further develop a method of the type mentioned above in such a way that a gentle treatment of the retained substance is achieved when pressure sensitive retained substances are separated while also requiring a smaller energy input for producing the pressure gradient.

For achieving this objective the above mentioned method is characterized according to the invention in that a reduced pressure is produced on the permeate side of the membrane by sucking off the permeate by means of a jet pump and by introducing the permeate into a closed circuit flow, whereby the permeate functions as a drive means for the jet pump whithin the closed circuit flow.

The supply of the suspension into the supply space or retention space can take place at a relatively low pressure because a reduced pressure is produced on the permeate side of the membrane, whereby the pressure gradient necessary for the separation is achieved completely or at least to a substantial extent by the production of the reduced pressure on the permeate side of the membrane. For the production of this reduced pressure and for the closed circuit guiding of the permeate, energy is also necessary. However, the sum of the energies required for producing the small excess pressure in the supply space or retention space and for the reduced pressure on the permeate side of the membrane is substantially smaller than in conventional methods for the production of the relative high excess pressure in the supply space or retention space when working with atmospheric pressure on the permeate side.

Due to the lower pressure difference between the supply side or retention side on the one hand and the atmosphere on the other hand, the retained substance is exposed to a respectively smaller pressure loading so that also relatively shear sensitive cells such as animal cells or fungi cultures growing in submersion, are not impaired or damaged by the pressure loading.

Further, a more uniform pressure distribution is achieved along the membrane due to producing the reduced pressure on the permeate side of the membrane on the one hand and the excess pressure on the supply side or retention side of the membrane on the other hand. Thus, a more uniform loading of the membrane and thus a higher efficiency is also achieved.

The new method is especially suitable for a sterile operation because the permeate used for the suction on the permeate side of the membrane and serving as a drive jet, has been previously withdrawn from the process.

Due to the suction on the permeate side of the membrane by means of the jet pump, substantial advantages are achieved as compared to the possible use of vacuum pumps, because undesired evaporations are avoided, or, if these evaporations should occur nevertheless, they are returned into the liquid phase without any additional measures.

The maximum reduced pressure achievable on the permeate side by means of the jet pump depends on the respective vapor pressure at the temperature of the permeate functioning as drive means in the closed circuit flow. For this reason it is suitable to cool the permeate during the closed circuit flow.

For performing the method the invention starts from known apparatuses which are equipped with a membrane filter arrangement and with devices for the supply of the suspension and for the retained substance discharge on the one side and which are also equipped with devices for the permeate discharge on the other side of the membrane. Such apparatuses also comprise a collecting container connected with the permeate discharge conduit. The collecting container is equipped with a discharge conduit and a level control for the permeate to be removed. Such an apparatus is characterized according to the invention in that the collecting container is arranged in series in a closed circuit flow conduit with a conveying pump and with a jet pump, and in that the permeate discharge conduit starting from the filter arrangement is connected with the jet pump. This apparatus is distinquished by a very simple construction and can be operated with a large yield, yet with a small energy input. In this connection it is suitable if the closed circuit conduit is passed through a cooling device which is suitably constructed as a heat exchanger so that the removed heat can be employed again in a useful way.

The described apparatus is especially useful for sterile processes which, however, required that the sterility is also maintained during the back rinse. For this purpose it is advantageous to provide a three-way valve having a back rinse conduit leading into the permeate discharge conduit between the conveying pump and the jet pump and to further provide a three-way valve for connecting the retained substance discharge conduit with a supply container or with a fermenter for the suspension.

Only in this manner is it possible to perform the back rinsing of the filter arrangement with the aid of the conveying pump and by means of the previously obtained permeate.

The present method will be described in more detail with reference to the drawing.

The drawing shows strictly in a schematic manner an example embodiment of an apparatus for performing the method according to the invention.

The drawing shows at 1 a fermenter which is equipped with a stirring mechanism 2 and which has an exit conduit 3 connected to a conveying pump 4. The conveying pump 4 pumps the suspension flowing out of the fermenter through a pressure conduit 5 into the membrane filter arrangement altogether designated by reference number 6. The membrane filter arrangement 6 is divided by the membrane 7 into a supply or retention space 6a and into a permeate space 6b. The supply conduit 5 leads into the supply or retention space 6a. The retained substance discharge conduit 8 is arranged opposite to the supply conduit 5. By means of a three-way valve 21 it is possible to selectively return the retained substance through the conduit 22 to the fermenter 1 or to remove it from the process at 23. The permeate space 6b is connected through a permeate discharge conduit 9 to a jet pump 10 which is arranged in the course of a closed circuit conduit altogether referred to by reference number 11. The closed circuit conduit 11 extends from the bottom side of a closed permeate collecting container 12 through a conduit section 11a to the suction side of the conveying pump 13 and from the pressure side of the conveying pump 13 through a further conduit section 11b to a cooling device 14 operating as a heat exchanger. A further conduit section 11c leads from the heat exchanger 14 to the jet pump 10 and a conduit section 11d leads form the jet pump 10 to the upper side of the permeate collecting container 12. The liquid level in the permeate collecting container 12 is indicated in the figure by a dashed line.

The permeate collecting container 12 is connected to a level control mechanism 15 by means of a permeate discharge conduit 16 which is connected through a three-way valve 17 with a conduit 18 for the further conveying of the permeate. The further conveying conduit 18 may also be connected directly with the conduit section 11b of the closed circuit conduit 11 through the valve 17.

In the operation of the described apparatus the suspension withdrawn from the fermenter 1 through the pump 4 is supplied through the conduit 5 to the membrane filter arrangement 6. The pump pressure in this connection produces a pressure in the supply or retention space 6a. This pressure can be adjusted to different values by control means not shown in the drawing.

In the operation of the apparatus the conveying of the already obtained permeate is accomplished by the pump 13 through the closed circuit conduit 11, whereby the permeate being conveyed in the closed circuit functions as a drive means for the jet pump 10. Due to the connection of the jet pump 10 through the permeate discharge conduit 9 with the permeate space 6b of the membrane filter arrangement 6 a reduced pressure is produced in the permeate space 6b. This reduced pressure is effective as a separation pressure in combination with the excess pressure produced by the conveying pump 4 on the supply or retention.

The permeate is conveyed through the jet pump 10 out of the permeate space 6b into the closed circuit conduit 11 and reaches the permeate collecting container 12 through the conduit section 11d. A respective portion of the permeate conducted in the closed circuit is removed from the container 12 as a function of level control, through the permeate discharge conduit 16 into the further conveying conduit 18.

Due to the production of the reduced pressure in the permeate space 6b of the membrane filter arrangement 6, it is possible to maintian the excess pressure required in the supply or retention space 6a correspondingly lower so that a gentle treatment is achieved of pressure sensitive or shearing force sensitive substances. Further, the energy input for producing the entire pressure difference in the membrane filter arrangement 6 can be substantially reduced in comparison to an operation with atmospheric pressure in the permeate space 6b.

A three-way valve 19 is arranged in the section 11c of the closed circuit conduit 11 for the purpose of a back rinsing of the membrane filter arrangement. The three-way valve 19 is connected through a back rinsing conduit 20 with the permeate discharge conduit 9 exiting from the membrane filter arrangement 6. A three-way valve 21 is also provided in the retained substance discharge conduit 8 for the back rinsing. The three-way valve 21 makes it possible to selectively return the rinsing medium to the fermenter 1 or to remove it from the process through a conduit 23.

For performing the back rinsing the three-way valve 19 in the conduit section 11c is so adjusted that it closes the supply to the jet pump 10 and that it connects the conduit section 11c with the back rinsing conduit 20. The three-way valve 21 in the retained substance discharge conduit 8 is customarily so adjusted that it connects the retained substance discharge conduit 8 with the conduit 22. In this position of the mentioned valves 19 and 21 the permeate is conveyed by the conveying pump 13 through the back rinsing conduit 20 into the permeate space 6b and through the membrane 7 into the supply or retention space 6a from where it reaches the discharge conduit 3 or the fermenter 1 through the retained substance discharge conduit 8 and the conduit 22. In this connection the conveying pump 4 may be temporarily switched off or a shut-off valve 24 may be provided in the supply conduit 5 so that during the back rinsing the supply of suspension to the membrane filter arrangement 6 may be interrupted.

We claim:

1. An apparatus for using membranes for separating liquids from a liquid fermentation suspension in a fermenter, comprising membrane filter means including a device for a suspension inflow and a device for an outflow of retained substance on one side of said membrane filter means, conduit means for discharging liquid permeate on the other side of said membrane filter means, a closed collecting container for liquid permeate connected to said permeate discharge conduit means, outflow conduit means connected to said closed collecting container for removing liquid permeate from said closed collecting container, level control means connected to said closed collecting container, a conveying pump, a jet pump, and conduit means connecting said closed collecting container with said conveying pump and said conveying pump with said jet pump, said permeate discharging conduit means being connected to said jet pump, said conduit means comprising a conduit section connecting said jet pump to said closed collecting container for forming a completely closed liquid permeate circulating circuit in which liquid permeate is supplied as a drive medium to said jet pump by said conveying pump, said apparatus further comprising a back rinsing conduit (20) having one end connected to said permeate discharging conduit means (9), a first three-way valve (19) connected between said conveying pump, said jet pump, and to the other end of said back rinsing conduit (20), and a second three-way valve (21) for connecting said retained substance outflow device to said fermenter.

2. An apparatus for filtering a liquid suspension containing pressure sensitive substances to be retained, comprising a membrane filter, a filter chamber divided by said membrane filter into a retention space (6a) and into a permeate space (6b), means for the supply of the liquid suspension into said retention space, means for removing the retained substance from said retention space, means for removing liquid permeate from said permeate space (6b), a closed collecting container (12) for collecting liquid permeate, first conduit means (9, 11d) connecting said closed collecting container (12) to said permeate space (6b), permeate discharge means (16, 17, 18) for removing liquid permeate from said closed collecting container (12), level control means cooperating with said closed collecting container for liquid permeate, closed circuit second conduit means (11a, 11b, 11c) connected to said closed collecting container (12), a conveying pump (13) connected in said closed circuit second conduit means, a jet pump (10) connected in said closed circuit second conduit means in such a position that said conveying pump (13) supplies liquid permeate to said jet pump (10) as a drive medium, said jet pump being also connected to said first conduit means (9, 11d) for providing a reduced pressure in said permeate space (6b) and for forming a completely closed liquid permeate circulation circuit out of said closed collecting container and back into said closed collecting container, and a cooling device (14) in said closed circuit second conduit means between said conveying pump means (13) and said jet pump (10) for preventing an evaporation of said liquid permeate in said completely closed liquid permeate circulation circuit.

3. The apparatus of claim 2, wherein said cooling device (14) is constructed as a heat exchanger.

4. The apparatus of claim 2, further comprising a three-way valve (19) between said conveying pump (13) and said jet pump (10) in said closed circulation circuit, a back rinsing conduit (20) leading from said three-way valve (19) into said first conduit means upstream of said jet pump (10).

5. The apparatus of claim 2, further comprising a retained substance discharge conduit (8), a supply container or a fermenter (1) for said liquid suspension, and valve means (21) for connecting said retained substance discharge conduit (8) to said supply container or fermenter (1).

* * * * *